United States Patent [19]
Uemura et al.

[11] Patent Number: 5,132,406
[45] Date of Patent: Jul. 21, 1992

[54] METHOD OF PRODUCING IMMUNOGLOBULIN PREPARATIONS FOR INTRAVENOUS INJECTION

[75] Inventors: Yahiro Uemura, Hirakata; Katuhiro Uriyu, Sakurai; Kazuo Takechi, Daito; Yutaka Hirao, Toyonaka; Tadakazu Suyama, Tsuzuki, all of Japan

[73] Assignee: The Green Cross Corporation, Osaka, Japan

[21] Appl. No.: 348,139

[22] Filed: May 5, 1989

Related U.S. Application Data

[63] Continuation of Ser. No. 52,370, May 19, 1987, abandoned.

[30] Foreign Application Priority Data

| May 19, 1986 | [JP] | Japan | 61-114421 |
| Sep. 30, 1986 | [JP] | Japan | 61-234757 |
| Jan. 31, 1987 | [JP] | Japan | 62-21481 |

[51] Int. Cl.$^5$ .................. A61K 39/395; C07K 3/28
[52] U.S. Cl. ................... 530/390.1; 424/85.8; 530/390.5
[58] Field of Search ............. 530/386, 381, 383, 385, 530/387, 413, 415, 416, 417, 420; 424/85.8, 101; 514/2, 8, 21

[56] References Cited

U.S. PATENT DOCUMENTS

| 3,869,436 | 3/1975 | Falksveden | 424/101 |
| 4,075,193 | 2/1978 | Campbell | 260/112 B |
| 4,093,606 | 6/1978 | Coval | 424/86 |
| 4,100,149 | 7/1978 | Meiller et al. | 530/416 |
| 4,124,576 | 11/1978 | Coval | 424/101 |
| 4,165,370 | 8/1979 | Coval | 424/85 |
| 4,256,631 | 3/1981 | Yokoo et al. | 530/387 |
| 4,272,521 | 6/1981 | Zuffi | 424/85.8 |
| 4,278,594 | 7/1981 | Amrani | 530/381 |
| 4,305,870 | 12/1981 | Liu et al. | 530/416 |
| 4,318,902 | 3/1982 | Stephan | 530/387 |
| 4,371,520 | 2/1983 | Uemura et al. | 530/387 |
| 4,440,679 | 4/1984 | Fernandes et al. | 530/387 |
| 4,499,073 | 2/1985 | Tenold | 424/85 |
| 4,606,825 | 8/1986 | Crane | 210/635 |
| 4,639,513 | 1/1987 | Hou et al. | 424/85 |
| 4,640,834 | 2/1987 | Eibl et al. | 530/383 |
| 4,664,913 | 5/1987 | Mielke et al. | 530/387 |
| 4,687,664 | 8/1987 | Philapitsch | 530/381 |
| 4,721,777 | 1/1988 | Uemura et al. | 424/85 |

FOREIGN PATENT DOCUMENTS

| 0035616 | 9/1981 | European Pat. Off. . |
| 0168506 | 1/1986 | European Pat. Off. . |
| 0196761 | 10/1986 | European Pat. Off. . |
| 8606727 | 11/1986 | Fed. Rep. of Germany . |

OTHER PUBLICATIONS

Kamimura, Patent Abstracts of Japan, vol. 10, No. 252, (C-369) [2308] JP-A-61 78 730, Aug. 29, 1986.
Kristiansen, Chem. Abstr., vol. 82, No. 3, p. 352, 14956w, Jan. 20, 1975.

*Primary Examiner*—Howard E. Schain
*Attorney, Agent, or Firm*—Fleit, Jacobson, Cohn, Price, Holman & Stern

[57] ABSTRACT

A method of producing immunoglobulin preparations for intravenous injection which starts with an immunoblobulin-containing fraction and comprises the treatment steps of:

(a) treating said fraction with 4-10 weight/volume percent of polyethylene glycol having a molecular weight of 1,000-10,000 under conditions of pH 4-6, ion strength 0.0001-0.1M and temperature 0°-4° C. and recovering the supernatant, (b) treating the supernatant obtained in step (a) with 10-15 weight/volume percent of polyethylene glycol having a molecular weight of 1,000-10,000 under conditions of pH 6-9, ion strength 0.0001-0.1M and temperature 0°-4° C. and recovering the resulting precipitate, and (c) heat-treating, in any desired step, said immunoglobulin in the presence of a stabilizer under conditions sufficient to inactivate contaminant viruses.

The preparations obtained according to the invention retain immunoglobulins without substantial inactivation thereof, and are substantially free of such contaminants as anti-human blood group substance antibodies. With contaminant viruses inactivated as a result of the heat treatment, said preparations have good solubility and are sufficiently low in anticomplement activity.

8 Claims, No Drawings

METHOD OF PRODUCING IMMUNOGLOBULIN PREPARATIONS FOR INTRAVENOUS INJECTION

RELATED APPLICATION

This is a continuation of Ser. No. 052,370, filed May 19, 1987, now abandoned.

TECHNICAL FIELD

This invention relates to a method of producing immunoglobulin preparations for intravenous injection.

DESCRIPTION OF THE PRIOR ART

Immunoglobulin preparations for intravenous injection have been so far in wide use in the prevention and treatment of infectious diseases, but since they are lacking in heat stability, they have never been heat-treated.

However, their contamination with viruses such as hepatitis virus cannot always be denied. Therefore, for inactivating contaminant viruses, a method comprising liquid-phase heat treatment [e.g. Japanese Laid-open Patent Application Kokai Tokkyo Koho No. Showa 61-191622] and a method comprising dry heat treatment [e.g. Japanese Laid-open Patent Application Kokai Tokkyo Koho No. Showa 61-78730 and Japanese Patent Application No. Showa 60-270195] have already been proposed.

OBJECT OF THE INVENTION

A primary object of the invention is to improve the above heat treatment method and thereby provide a method of producing immunoglobulin preparations for intravenous injection, which are highly safe and effective and therefore applicable for clinical purposes.

In line with this object, the present inventors made investigations in order to establish an industrial method of producing such preparations. As a result of combination of a step of fractionation treatment with polyethylene glycol (hereinafter referred to as PEG), a step of heat treatment and other steps and of elaboration of treatment conditions for each step, the present invention has been completed.

SUMMARY OF THE INVENTION

The gist of the invention is as described in the accompanying claims and the invention provides a method of producing immunoglobulin preparations for intravenous injection particularly starting with an immunoglobulin-containing fraction and comprising the step of:

(a) treating said fraction with PEG having a molecular weight of 1,000-10,000 under conditions of pH 4-6, ion strength 0.0001-0.1M and temperature 0°-4° C. and recovering the supernatant, (b) treating the supernatant obtained in step (a) with 10-15 weight/volume percent of PEG having a molecular weight of 1,000-10,000 under conditions of pH 6-9, ion strength 0.0001-0.1M and temperature 0°-4° C. and recovering the resulting precipitate, and (c) heat-treating, in any desired step, the above immunoglobulin in the presence of a stabilizer under conditions sufficient to inactivate contaminant viruses.

DETAILED DESCRIPTION OF THE INVENTION

(1) Starting Material

In the practice of the invention, an immunoglobulin-containing fraction is used as the starting material. This is not limited to any particular fraction provided that it is a human plasma-derived fraction containing immunoglobulin. More specifically, there may be mentioned the fractions II+III and II obtained by ethanol fractionation according to Cohn and immunoglobulin-containing paste-form fractions equivalent thereto. The starting material may contain human blood group antibodies, kallikrein, prekallikrein, IgM and IgG in polymer form, and the like.

(2) Production Method

The production method according to the invention preferably comprises the following treatment steps:

1) Low-concentration PEG Treatment Step

In this step, the starting material is treated with low-concentration PEG and the supernatant is recovered.

The starting material is suspended in an appropriate aqueous solvent. The aqueous solvent may contain such solutes as sodium chloride, sodium phosphate, potassium phosphate, acetic acid, sodium acetate, citric acid and sodium citrate.

This suspension is treated with PEG having a molecular weight of 1,000-10,000 (preferably about 2,000-6,000) by such means as mixing both. The treatment conditions should preferably be 4-10 weight/volume percent PEG concentration (more preferably 4-8 weight/volume percent), pH4-6 (more preferably 4.5-5.5) and 0.0001-0.1M ion strength (more preferably 0.0001-0.01M).

On that occasion, it is preferable that the protein concentration be 1-20 weight/volume percent (more preferably 5-15 weight/volume percent).

Said treatment is generally carried out by stirring at about 0°-4° C. for about 30 minutes to about 6 hours.

Thereafter, the supernatant is recovered by, for example, centrifugation (6,000-8,000 rpm, 10-30 minutes).

2) High-concentration PEG Treatment Step

In this step, the supernatant obtained in step 1) is treated with high-concentration PEG and the precipitate is recovered.

The above supernatant is treated further with PEG having a molecular weight of 1,000-10,000 (preferably 2,000-6,000) by such means as mixing both. The treatment conditions should preferably be 10-15 weight/volume percent PEG concentration (more preferably about 11-13 weight/volume percent), pH 6-9 (more preferably 7.5-8.5) and 0.0001-0.1M ion strength (more preferably 0.0001-0.01M).

On that occasion, it is preferable that the protein concentration be 1-20 weight/volume percent (more preferably 5-15 weight/volume percent).

Said treatment is generally carried out by stirring at about 0°-4° C. for about 30 minutes to about 6 hours.

Thereafter, the resultant precipitate is recovered by, for example, centrifugation (6,000-8,000 rpm, 10-30 minutes).

3) Anion Exchanger Treatment Step

In this step, after the precipitate fraction obtained in step 2) is dissolved in an aqueous solvent, or after the treatment in step 5) to be mentioned later herein, the solution is treated by contacting with an anion exchanger, whereby the unadsorbed fraction is recovered.

This step is conducted for the purpose of removing IgM and IgG polymers.

[i] Preparation of the Anion Exchanger

The anion exchanger is an insoluble carrier having an anion exchanging group bonded thereto. Usable examples of the anion exchanging group are diethylaminoethyl (DEAE) and quaternary aminoethyl (QAE) and usable examples of the insoluble carrier are agarose, cellulose, dextran and polyacrylamide.

The binding can be effected by an appropriate known method.

[ii] Treatment Method

The precipitate fraction obtained in step 2) is dissolved in an appropriate aqueous solvent. The aqueous solvent should preferably be an aqueous solution having a pH of 5-8 (more preferably 5.5-7.5) and a low ion strength (preferably 0.01-0.2M). It may contain such solutes as those mentioned for the aqueous solvent to be used in step 1). The protein concentration should preferably be 1-15 weight/volume percent (more preferably 3-10 weight/volume percent).

The solution is brought into contact with the anion exchanger equilibrated with the above-mentioned aqueous solvent. For this treatment, both the batch method and the column method can be used.

In the batch method, for instance, the solution to be treated is mixed with the anion exchanger in an amount of about 10-100 ml per milliliter of the anion exchanger. The mixture is stirred at 0°-4° C. for about 30 minutes to about 2 hours and then centrifuged (6,000-8,000 rpm, 10-30 minutes), whereby the supernatant is recovered.

In the column method, too, about 10-100 ml of the solution to be treated is brought into contact with each milliliter of the anion exchanger and the unadsorbed fraction is recovered.

This step, namely step 3), can be omitted if desired. In cases where liquid-phase heat treatment is performed, it is preferable to carry out said anion exchange treatmnet after the immobilized human blood group substance treatment in step 5).

4) Treatment with an Immobilized Diamino Compound

In this step, the precipitate fraction obtained in step 2) or the unadsorbed fraction obtained in step 3) is brought into contact with an immobilized diamino compound and the unadsorbed fraction is recovered.

This step is performed for the purpose of removing prekallikrein and/or kallikrein.

[i] Preparation of the Immobilized Diamino Compound

The immobilized diamino compound is a diamino compound immobilized on an insoluble carrier.

As usable diamino compounds, there may be mentioned aminobenzamidine, aminobenzoguanidine, lysine and arginine.

As the insoluble carrier, there may be mentioned agarose, cellulose, dextran, silica gel, glass, and so on.

The immobilization can be carried out by a known method. For example, the diamino compound can be immobilized on agarose, cellulose and the like by the CNBr activation method and on silica gel, glass and the like by the oxirane method.

[ii] Treatment Method

The material to be treated, for example the unadsorbed fraction from step 3), is brought into contact with the immobilized diamino compound under conditions of pH 5-8 (preferably 6-7) and ion strength 0.01-0.2M (preferably 0.05-0.15M). On that occasion, the protein concentration should preferably be 1-15 weight/volume percent (more preferably 3-10 weight/volume percent) and both the batch method and the column method can suitably be used.

In the batch method, the above-mentioned fraction is mixed with the immobilized diamino compound in an amount of about 10-100 ml per milliliter of the diamino compound and the mixture is stirred at 0°-10° C., preferably 0°-4° C., for 30 minutes to 4 hours, preferably about 30 minutes to about 2 hours, and then the supernatant is recovered by centrifugation (6,000-8,000 rpm, 10-30 minutes).

In the column method, too, about 10-100 ml of the above fraction is brought into contact with each milliliter of the immobilized diamino compound and the unadsorbed fraction is recovered.

This step, namely step 4), can be omitted as desired.

5) Immobilized Human Blood Group Substance Treatment Step

In this step, the precipitate fraction obtained in step 2), the unadsorbed fraction obtained in step 3) or the unadsorbed fraction obtained in step 4) is treated by bringing the same into contact with immobilized human blood group substances and the unadsorbed fraction is recovered.

This step is performed for the purpose of removing human blood group antibodies.

[i] Preparation of Immobilized Human Blood Group Substances

The immobilized human blood group substances are human blood group substances immobilized on an insoluble carrier.

The human blood group substances can be prepared by a known method. For example, they can be obtained by lysing or sonicating human erythrocytes of the group A, B, AB or O in a hypotonic solution and then purifying by the ammonium sulfate or PEG fractionation method.

Furthermore, the human blood group substances are dissolved in physiological saline and heat-treated under conditions said to be effective to inactivate contaminant viruses, for example at about 50°-70° C., preferably at about 60° C., for 7-13 hours, preferably for about 10 hours or at about 80°-130° C., preferably at 95°-121° C., for about 1-40 minutes, preferably for about 2-30 minutes. Then the insoluble matter is removed by centrifugation. The subsequent dialysis against distilled water gives each human blood group substance.

On the other hand, agarose, cellulose, dextran, silica gel, glass and the like may be used as the insoluble carrier.

The immobilization can be carried out by a known method. For example, the human blood group substances can be immobilized on agarose, cellulose and the like by the CNBr activation method and on silica gel, glass and the like by the oxirane method.

[ii] Treatment Method

The material to be treated, for example the unadsorbed fraction obtained in step 4), is brought into contact with the immobilized human blood group substances equilibrated with the above-mentioned aqueous solvent under conditions of pH 5-8 (preferably 6-7) and ion strength 0.01-0.2M (preferably 0.05-0.15M). On that occasion, the protein concentration should be preferably 1-15 weight/volume percent (more preferably 3-10 weight/volume percent) and both the batch method and the column method can be used.

In the batch method, for instance, about 10-100 ml of the solution to be treated is mixed with each milliliter of the immobilized human blood group substances and the mixture is stirred at 0°-10° C., preferably 0°-4° C., for 30 minutes to 4 hours, preferably about 30 minutes to about 2 hours and then centrifuged (6,000-8,000 rpm, 10-30 minutes), whereby the supernatant is recovered.

In the column method, too, about 10-100 ml of the solution to be treated is brought into contact with each milliliter of the immobilized human blood group substances and the unadsorbed fraction is recovered.

6) Heat Treatment Step

In this step, heat treatment is carried out in the presence of a stabilizer under such conditions that the loss in the antibody activity of immunoglobulins can be minimized but that contaminant viruses, such as HB virus and AIDS virus, can be completely inactivated. This heat treatment may be conducted in any desired stage, that is, it may be conducted to the aforesaid starting materials or in the stages between any two of the aforesaid steps (1)-(5) or after completing the said steps (1)-(5). The heat treatment is carried out in a dry condition in which the moisture content is not higher than 3% (i.e. dry heat treatment) or in a solution state, namely in the state of an aqueous solution of immunoglobulins (i.e. liquid-phase heat treatment). The liquid-phase heat treatment is preferable and recommendable.

In both cases, the stabilizer is preferably a disaccharide (e.g. saccharose, maltose) or a sugar alcohol (e.g. sorbitol, mannitol), for instance. Most preferred is sorbitol.

In a preferred embodiment, the level of addition of the stabilizer is as follows: For dry heat treatment, it is a suitable example to use a disaccharide and/or sugar alcohol in an amount of 0.5-5 weight/volume percent (more preferably 1-3 weight/volume percent) and for liquid-phase heat treatment, in an amount of not less than 10 weight/volume percent (more preferably 30-40 weight/volume percent).

The concentration of immunoglobulins to be treated by dry heating is suitably adjusted to 1-10 weight/volume percent (preferably 3-7 weight/volume percent) as proteins. In the case of liquid-phase heat treatment, said concentration is preferably adjusted to 0.1-30 weight/volume percent (more preferably 5-20 weight/volume percent) as proteins.

In the case of dry heat treatment, the heat treatment is carried out after addition of a stabilizer, sterilization by filtration, which is optional, and reduction of the moisture content to not higher than 3%, preferably not higher than 1%, by lyophilization, for instance. Drying is performed, for example, under vacuum (0.5 mm Hg) at 20°-40° C. for about 24-96 hours. The heat treatment is then carried out, for example, at 50°-70° C. (preferably about 60° C.) for 10-200 hours (preferably 50-100 hours).

The stability of the material during heating can be improved by performing this heat treatment step in an inert gas atmosphere. As the inert gas, there may be mentioned, for example, nitrogen gas, argon and helium.

In the case of liquid-phase heat treatment, the aqueous solution is adjusted to pH 4.5-6.5, preferably pH 5-6, and treated, for example, at 50°-70° C. (preferably about 60° C.) for 10 minutes to 20 hours (preferably about 10 hours).

In the case of dry heat treatment, the heat treatment is preferably conducted in the final step, for example after step 5).

In the case of liquid-phase heat treatment, it is suitable to subject the starting material to the heat treatment or to carry out said treatment after step 2). When said treatment is carried out after step 2), it is preferable, from the viewpoint of the contaminant removal, to repeat steps 1) and 2).

The preparations obtained in accordance with the invention, when to be used, are dissolved in an appropriate solvent (e.g. distilled water for injection) and used for the prevention or treatment of infectious diseases and other diseases by intravenous injection or drip infusion, for instance.

The preparations obtained in accordance with the invention retain immunoglobulins with almost no inactivation thereof, and are free of such contaminants as anti-human blood group substance antibodies. Furthermore, with contaminant viruses being inactivated as a result of heat treatment, said preparations have good solubility, sufficiently low anticomplement activity and other desirable properties. Therefore, they are safe preparations meeting the requirements of the 1985 edition of the Japanese Standards for Biological Preparations.

Thus, the method according to the invention is useful as an industrial method of producing immunoglobulin preparations for intravenous injection.

EXAMPLE 1

To 1 kg of Cohn's fractions II+III, there was added 10 liter of 0.001M sodium chloride solution. The resultant solution was adjusted to pH 5.0 and then PEG #4000 was added to a final concentration of 8 weight/volume percent. The mixture was then centrifuged at 2° C.

The thus-obtained supernatant was adjusted to pH 8.0 with 1N sodium hydroxide, and then PEG #4000 was added to a final concentration of 12 weight/volume percent. The resultant mixture was centrifuged at 2° C. and an IgG fraction was collected.

This IgG fraction was dissolved in 0.6 weight/volume percent sodium chloride solution to an IgG concentration of 7 weight/volume percent, and the solution was adjusted to pH 6.5.

A 100-ml portion of this IgG solution was passed through a column of 5 ml of Benzamidine-Sepharose (registered trademark; Pharmacia) and a column of 3 ml of human blood group substance-bearing Formyl-Cellulofine (registered trademark; Seikagaku Kogyo: chemically modified cellulose whose hydroxide group is substituted by a formyl group), whereby human blood group antibodies were adsorbed and removed. As a result of adsorption in this step, the blood group antibody level decreased from (1:32) to (1:2).

To the unadsorbed fraction were added 1 weight-/volume percent of human albumin and 2 weight-/volume percent of saccharose per 5 weight/volume percent IgG solution. The resultant mixture was sterilized by filtration and lyophilized.

The lyophilizate was then heat-treated at 60° C. for 72 hours to give an immunoglobulin preparation for intravenous injection.

This preparation substantially contained monomeric IgG alone. The human blood group antibody content was satisfactorily low and the anticomplement value was about 10–15 $CH_{50}$/ml.

The preparation was highly soluble and met the requirements, relative to immunoglobulin preparations for intravenous injection, of the Japanese Biological Preparations Standards.

EXAMPLE 2

A paste of Cohn's fraction II was treated in the same manner and an equivalent preparation was obtained.

EXAMPLE 3

To 1 kg of Cohn's fractions II+III, there was added 10 liters of 0.001M sodium chloride solution. After the pH was adjusted to 5.0, PEG #4000 was added to a final concentration of 8 weight/volume percent, and the resultant mixture was centrifuged at 2° C.

The thus-obtained supernatant was adjusted to pH 8.0 with 1N sodium hydroxide, and PEG #4000 was then added to a final concentration of 12 weight/volume percent, and the mixture was centrifuged at 2° C. An IgG fraction was thus collected.

This IgG fraction was dissolved in water to an IgG concentration of 10 weight/volume percent. Sorbitol was added in an amount of 50 g per 100 ml of the 10 weight/volume percent IgG solution. The resultant solution was heat-treated at 60° C. for 10 hours.

After heating, the pH was adjusted to 6.8, PEG #4000 was added to a final concentration of 6 weight-/volume percent, and the mixture was centrifuged at 2° C.

The supernatant obtained was adjusted to pH 8.0 with 1N sodium hydroxide, and PEG #4000 was then added to a final concentration of 12 weight/volume percent, and the mixture was centrifuged at 2° C. An IgG fraction was thus obtained as a precipitate fraction.

To a solution of this fraction was added DEAE-Sephadex (1 ml per 50 ml of solution). After contacting treatment at 0°–4° C. for about 1 hour, the supernatant (IgG solution) was recovered by centrifugation (7,000 rpm, about 20 minutes). A 100-ml portion of this IgG solution was passed through a cloumn of 5 ml of Benzamidine-Sepharose (registered trademark; Pharmacia) and a column of 3 ml of human blood group substance-bearing Formyl-Cellulofine, whereby human blood group antibodies were adsorbed and removed. The adsorption in this step reduced the blood group antibody level from (1:32) to (1:2).

The IgG fraction was dialyzed against isotonic physiological saline, sterilized by filtration and lyophilized to give an immunoglobulin preparation for intravenous injection.

This preparation substantially contained monomeric IgG alone. The human blood group antibody content was satisfactorily low and the anticomplement value was about 10–15 $CH_{50}$/ml.

The preparation was highly soluble and met the requirements, relative to immunoglobulin preparations for intravenous injection, of the Japanese Biological Preparations Standards.

EXAMPLE 4

To 1 kg of Cohn's fractions II+III, there was added 10 liters of 0.001M sodium chloride solution, and further added sorbitol in an amount of 50 g per 100 ml of the solution. The resultant solution was adjusted to pH 5.5 and heat-treated at 60° C. for 10 hours.

After heat treatment, the pH was adjusted to 5.5, and PEG #4000 was added to a final concentration of 4 weight/volume percent, and the mixture was centrifuged at 2° C.

After the supernatant obtained was adjusted to pH 8.8 with 1N sodium hydroxide, PEG #4000 was added to a final concentration of 15 weight/volume percent, and the mixture was centrifuged at 2° C. to give an IgG fraction as a precipitate fraction.

To a solution of this fraction was added DEAE-Sephadex (1 ml per 50 ml of the solution). After the mixture was treated for contacting at 0°–4° C. for about 1 hour, the supernatant (IgG solution) was recovered by centrifugation (7,000 rpm, about 20 minutes).

A 100-ml portion of this IgG solution was passed through a column of 5 ml of Benzamidine-Sepharose (registered trademark; Pharmacia) and a column of human blood group substance-bearing Formyl-Cellulofine, whereby human blood group antibodies were adsorbed and removed. The adsorption in this step reduced the blood group antibody level from (1:32) to (1:2).

The IgG fraction was dialyzed against isotonic physiological saline, sterilized by filtration and lyophilized to give an immunoglobulin preparation for intravenous injection.

This preparation substantially contained monomeric IgG alone. The human blood group antibody content was satisfactorily low and the anticomplement value was about 10–15 $CH_{50}$/ml.

The preparation was highly soluble and met the requirements, relative to immunoglobulin preparations for intravenous injection, of the Japanese Biological Preparations Standards.

EXAMPLE 5

To 1 kg of Cohn's fractions II+III, there was added 10 liters of water, and further added 50 g per 100 ml of sorbitol. The resultant solution was adjusted to pH 5.5 and then heat-treated at 60° C. for 10 hours.

After heat treatment, the pH was adjusted to 5.5, PEG #4000 was then added to a final concentration of 4 weight/volume percent, and the mixture was centrifuged at 2° C.

After the supernatant obtained was adjusted to pH 8.8 with 1N sodium hydroxide, PEG #4000 was then added to a final concentration of 15 weight/volume percent, and the mixture was centrifuged at 2° C. to give an IgG fraction as a precipitate fraction.

This precipitate was dissolved in an aqueous solvent, and to the solution DEAE-Sephadex was added (1 ml per 50 ml of the solution). After contacting treatment at 0°–4° C. for about 1 hour, the mixture was centrifuged (7,000 rpm, about 20 minutes) and the supernatant (IgG solution) was recovered.

A 100-ml portion of this IgG solution was passed through a column of 3 ml of human blood group substance-bearing Formyl-Cellulofine for the purpose of removing human blood group antibodies. The adsorption in this step reduced the blood group antibody level from (1:32) to (1:2).

The IgG fraction was dialyzed against isotonic physiological saline, sterilized by filtration and lyophilized to give an immunoglobulin preparation for intravenous injection.

This preparation substantially contained monomeric IgG alone. The human blood group antibody content was satisfactorily low and the anticomplement value was about 10-15 $CH_{50}$/ml.

The preparation was highly soluble and met the requirements, relative to immunoglobulin preparations for intravenous injection, of the Japanese Biological Preparations Standards.

EXAMPLE 6

To 1 kg of Cohn's fractions II+III, there was added 3 liters of water, and further added sorbitol in an amount of 50 g per 100 ml. The resultant solution was adjusted to pH 5.5 and then heat-treated at 60° C. for 10 hours.

After heat treatment, the pH was adjusted to 5.5, PEG #4000 was then added to a final concentration of 6 weight/volume percent, and after 3 hours of extraction at 2° C., the mixture was centrifuged at 2° C.

After the supernatant obtained was adjusted to pH 8.8 with 1N sodium hydroxide, PEG #4000 was added to a final concentration of 12 weight/volume percent, and the mixture was centrifuged at 2° C. to give an IgG fraction as a precipitate fraction. This precipitate was dissolved in distilled water. A 100-ml portion of the resultant IgG solution was passed through a column of 3 ml of human blood group substance-bearing Formyl-Cellulofine equilibrated with distilled water to thereby remove human blood group antibodies by adsorption. The adsorption in this step reduced the blood group antibody level from (1:32) to (1:2). To the solution was added DEAE-Sephadex (2 ml per 50 ml of the solution) equilibrated with 0.4% aqueous sodium chloride solution. After contact treatment at 0°-4° C. for about 1 hour, the DEAE-Sephadex was removed by filtration and the filtrate (IgG solution) was recovered.

In the IgG fraction were dissolved sorbitol (to a concentration of 2 weight/volume percent), NaCl (to 0.5 weight/volume percent) and albumin (to 1 weight/volume percent). The resultant solution was adjusted to pH 6.8, sterilized by filtration and lyophilized to give a immunoglobulin preparation for intravenous injection.

This preparation substantially contained monomeric IgG alone. The human blood group antibody content was satisfactorily low and the anticomplement value was about 10-15 $CH_{50}$/ml.

The preparation was highly soluble and met the requirements, relative to immunoglobulin preparations for intravenous injection, of the Japanese Biological Preparations Standards.

What is claimed:

1. A method of producing, for intravenous injection, an immunoglobulin preparation substantially free from agglutinative immunoglobulin and wherein any virus is inactivated, the method comprising;
   a) heat-treating an immunoglobulin-containing fraction in a solution state in the presence of at least 10 weight/volume percent of sorbitol, as stabilizer, at a pH from 4.5 to 6.5 under conditions sufficient to inactivate any contaminant virus;
   b) treating the fraction with from 4 to 10 weight/volume percent of polyethylene glycol (PEG) at a pH of from 4 to 6 and at a temperature of from 0° to 4° C., the PEG having a molecular weight of from 1,000 to 10,000 and an ion strength of from 0.0001 to 0.1M, and recovering thus-obtained supernatant,
   c) treating the obtained supernatant with from 10 to 15 weight/volume percent of PEG at a pH of from 6 to 9 and at a temperature of from 0° to 4° C., the PEG having a molecular weight of from 1,000 to10,000 and an ion strength of from 0.0001 to 0.1M, and recovering resulting precipitate, and then,
   d) dissolving the precipitate in an aqueous solvent having a pH of from 5 to 8, treating the resulting solution with an anion exchanger, and recovering the resulting unadsorbed fraction.

2. A method which consists essentially of the steps claimed in claim 1 in combination with treating said resulting unadsorbed fraction with an immobilized human blood group substance at a pH of from 5 to 8, and recovering the resulting unadsorbed fraction.

3. A method which consists essentially of the steps claimed in claim 1 in combination with treating said resulting unadsorbed fraction with an immobilized diamino compound at a pH of from 5 to 8 and, and recovering the thus-obtained unadsorbed fraction.

4. A method as claimed in claim 1 which consist essentially of:
   a) heat-treating the immunoglobulin-containing fraction in solution state in the presence of a stabilizer under conditions sufficient to inactivate any contaminant virus,
   b) treating said fraction with from 4 to 10 weight/volume percent of PEG at a pH of from 4 to 6 and at a temperature of from 0° to 4° C., the PEG having a molecular weight of from 1,000 to 10,000 and an ion strength of from 0.0001 to 0.1M, and recovering thus-obtained supernatant,
   c) treating the obtained supernatant with from 10 to 15 weight/volume percent of PEG at a pH of from 6 to 9 and at a temperature of from 0° to 4° C., the PEG having a molecular weight of from 1,000 to 10,000 and an ion strength of from 0.0001 to 0.1M, and recovering resulting precipitate,
   d) dissolving the precipitate in an aqueous solvent, having a pH of from 5 to 8 and, treating the resulting solution with an anion exchanger, and recovering the resulting unadsorbed fraction,
   e) treating the unadsorbed fraction, at a pH of from 5 to 8, with an immobilized diamino compound having and recovering the thus-obtained unadsorbed fraction, and
   f) treating the unadsorbed fraction from (e), at a pH of from 5 to 8, with an immobilized human blood group substance and recovering the resulting unadsorbed fraction.

5. A method as claimed in claim 1 which consist essentially of:
   a) treating an immunoglobulin-containing fraction with from 4 to 10 weight/volume percent of polyethylene glycol having a molecular weight of from 1,000 to 10,000 under conditions of pH from 4 to 6, ion strength from 0.0001 to 0.1M and temperature from 0° to 4° C., and recovering thus-obtained supernatant, b) treating the supernatant obtained in step (a) with from 10 to 15 weight/volume percent of polyethylene glycol having a molecular weight of from 1,000 to 10,000 under conditions of pH from 6 to 9, ion strength from 0.0001 to 0.1M and temperature from 0° to 4° C., and recovering resulting precipitate, c) dissolving the precipitate from step (b) in an aqueous solvent, and heat-treating the resulting solution (in solution state) in the presence of a stabilizer under conditions sufficient to inactivate any contaminant virus, d) treating said precipitate from step (c) with from 4 to 10 weight/volume percent of polyethylene glycol having a molecular weight of from 1,000 to 10,000 under conditions of pH from 4 to 6, ion strength from 0.0001 to 0.1M and temperature from 0° to 4° C., and recovering thus-obtained supernatant, e) treating the supernatant obtained in step (d) with from 10 to 15 weight/volume percent of polyethylene glycol having a molecular weight of from 1,000 to 10,000 under conditions of pH from 6 to 9, ion strength from 0.0001 to 0.1M and temperature from 0° to 4° C., and recovering resulting precipitate, f) dissolving the precipitate obtained in step (e) in an aqueous solvent, and treating the resulting solution with an anion exchanger under conditions of pH from 5 to 8, followed by recovery of the resulting unadsorbed fraction, g) treating the unadsorbed fraction from step (f) with an immobilized diamino compound under conditions of pH from 5 to 8, followed by recovery of the resulting unadsorbed fraction, and then h) treating the fraction from step (g) with an immobilized human blood group substance under conditions of pH from 5 to 8, followed by recovery of the resulting unadsorbed fraction.

6. A method as claimed in claim 1 which consist essentially of:

a) heat-treating an immunoglobulin-containing fraction in a solution state in the presence of the stabilizer under conditions sufficient to inactivate any contaminant virus, b) treating the heat-treated fraction from step (a) with from 4 to 10 weight/volume percent of polyethylene glycol having a molecular weight of from 1,000 to 10,000 under conditions of pH from 4 to 6, ion strength from 0.0001 to 0.1M and temperature from 0° to 4° C., and recovering thus-obtained supernatant, c) treating the supernatant obtained in step (b) with from 10 to 15 weight/volume percent of polyethylene glycol having a molecular weight of from 1,000 to 10,000 under conditions of pH from 6 to 9, ion strength from 0.0001 to 0.1M and temperature from 0° to 4° C., and recovering resulting precipitate, d) dissolving the precipitate obtained in step (c) in an aqueous solvent, and treating the resulting solution with an anion exchanger under conditions of pH from 5 to 8, followed by recovery of resulting unadsorbed fraction, and then e) treating the unadsorbed fraction from step (d) with an immobilized human blood group substance at a pH of from 5 to 8, followed by recovery of resulting unadsorbed fraction.

7. A method of producing, for intravenous injection, an immunoglobulin preparation substantially free from agglutinative immunoglobulin and wherein any virus is inactivated, the method consisting essentially of:

a) heating-treating an immunoglobulin-containing fraction in a solution state in the presence of at least 10 weight/volume percent of sorbitol, as stabilizer, at a pH from 4.5 to 6.5 under conditions sufficient to inactivate any contaminant virus;

b) treating the fraction with from 4 to 10 weight/volume percent of polyethylene glycol (PEG) at a pH of from 4 to 6 and at a temperature of from 0° to 4° c., the PEG having a molecular weight of from 1,000 to 10,000 and an ion strength of from 0.0001 to 0.1M, and recovering thus-obtained supernatant, c) treating the obtained supernatant with from 10 to 15 weight/volume percent of PEG at a pH of from 6 to 9 and at a temperature of from 0° to 4° C., the PEG having a molecular weight of from 1,000 to 10,000 and an ion strength of from 0.0001 to 0.1M, and recovering resulting precipitate, and then, d) dissolving the precipitate in an aqueous solvent having a pH of from 5 to 8, treating the resulting solution with an anion exchanger, and recovering the resulting unadsorbed fraction.

8. A method of producing, for intravenous injection, an immunoglobulin preparation substantially free from agglutinative immunoglobulin and wherein any virus is inactivated, the method consisting essentially of:

a) heat-treating an immunoglobulin-containing fraction in a solution state in the presence of from 10 to 40 weight/volume percent of a sorbitol at a pH from 4.5 to 6.5 under conditions sufficient to inactivate any contaminant virus, b) treating said fraction with from 4 to 10 weight/volume percent of polyethylene glycol having a molecular weight of from 1,000 to 10,000 under conditions of pH from 4 to 6, ion strength from 0.0001 to 0.1M and temperature from 0° to 4° C., and recovering thus-obtained supernatant, c) treating the supernatant obtained in step (b) with from 10 to 15 weight/volume percent of polyethylene glycol having a molecular weight of from 1,000 to 10,000 under conditions of pH from 6 to 9, ion strength from 0.0001 to 0.1M and temperature from 0° to 4° C. and recovering resulting precipitate, d) dissolving the precipitate obtained in step (c) in an aqueous solvent, and treating the solution with an immobilized human blood group substance under conditions of pH from 5 to 8, followed by recovery of the resulting unadsorbed fraction, and then e) treating the fraction from step (d) with an anion exchanger under conditions of pH from 5 to 8, followed by recover of the resulting unadsorbed fraction.

* * * * *